(12) United States Patent
Ko

(10) Patent No.: US 12,714,886 B2
(45) Date of Patent: Aug. 25, 2026

(54) HIFU DEVICE CAPABLE OF THREE-DIMENSIONAL TREATMENT, CONTROL METHOD THEREOF, AND TREATMENT METHOD USING THE SAME

(71) Applicant: LUTRONIC CORPORATION, Goyang-si (KR)

(72) Inventor: Kwangchon Ko, Goyang-si (KR)

(73) Assignee: LUTRONIC CORPORATION, Goyang-si (KR)

( * ) Notice: Subject to any disclaimer, the term of this patent is extended or adjusted under 35 U.S.C. 154(b) by 107 days.

(21) Appl. No.: 18/493,505

(22) Filed: Oct. 24, 2023

(65) Prior Publication Data

US 2024/0149079 A1 May 9, 2024

(30) Foreign Application Priority Data

Nov. 4, 2022 (KR) ........................ 10-2022-0145891

(51) Int. Cl.
*A61B 7/02* (2006.01)
*A61N 7/02* (2006.01)
*A61N 7/00* (2006.01)

(52) U.S. Cl.
CPC ........ *A61N 7/02* (2013.01); *A61N 2007/0078* (2013.01)

(58) Field of Classification Search
CPC ...... A61B 2090/065; A61N 2007/0034; A61N 2007/0078; A61N 2007/0091; A61N 2007/027; A61N 7/02; A61N 7/022
See application file for complete search history.

(56) References Cited

U.S. PATENT DOCUMENTS

| | | | | |
|---|---|---|---|---|
| 9,782,608 | B2 | 10/2017 | Qian et al. | |
| 2007/0167813 | A1 | 7/2007 | Lee et al. | |
| 2016/0332006 | A1 | 11/2016 | Slayton et al. | |
| 2017/0209717 | A1* | 7/2017 | Bonutti | A61B 34/76 |

FOREIGN PATENT DOCUMENTS

| | | | |
|---|---|---|---|
| EP | 4 079 373 | A1 | 10/2022 |
| KR | 10-1246557 | B1 | 3/2013 |

OTHER PUBLICATIONS

The Extended European Search Report for European Patent Application No. 23207729.7, dated Mar. 27, 2024.

* cited by examiner

*Primary Examiner* — Mark D Remaly

(57) ABSTRACT

Disclosed are a high-intensity focused ultrasound (HIFU) device capable of the three-dimensional treatment, a control method thereof and a treatment method using the same, in which treatment spots are formed along a circular path by rotating ultrasound transducers during skin treatment, thereby enabling three-dimensional treatment.

8 Claims, 21 Drawing Sheets

HIFU DEVICE CAPABLE OF THREE-DIMENSIONAL TREATMENT, CONTROL METHOD THEREOF, AND TREATMENT METHOD USING THE SAME

CROSS-REFERENCE TO RELATED APPLICATIONS

This application claims priority to Korean Patent Applications No. 10-2022-0145891 filed on Nov. 4, 2022 in Korea, the entire contents of which are hereby incorporated by reference in their entirety.

TECHNICAL FIELD

The disclosure relates to a high-intensity focused ultrasound (HIFU) device capable of three-dimensional treatment, a control method thereof, and a treatment method using the same, in which the focal depth and location of a transducer is adjustable to three-dimensionally treat tissue.

BACKGROUND ART

Tissue treatment using high-intensity focused ultrasound (HIFU) has been generally used to treat cancer cells, but recently developed and used as technology to regenerate tissue by irradiating skin with the HIFU.

In a conventional skin treatment device using the HIFU, a transducer is exposed to a liquid environment and operated to transfer energy to a single focal point in order to increase transfer efficiency in consideration of the characteristics of ultrasound when ultrasound is transferred through a medium. Regarding such a conventional HIFU treatment device, Korean Patent No. 1246557 has been disclosed.

However, such a conventional HIFU treatment device has a problem of lengthening treatment time and increasing patient discomfort because a user needs to move a handpiece repeatedly in order to perform treatment for various depths and large areas.

DISCLOSURE

Technical Problem

To solve the problems of conventional HIFU devices, an aspect of the disclosure is to provide a high-intensity focused ultrasound (HIFU) device capable of three-dimensional treatment, a control method thereof, and a treatment method using the same.

Technical Solution

According to an embodiment of the disclosure, there is provided a high-intensity focused ultrasound (HIFU) device capable of three-dimensional treatment, including: a body including a power supply and a controller; and a handpiece connected to the body and including a plurality of transducers configured to generate HIFU, the handpiece including a rotary actuator configured to rotate at least one of the transducers.

Meanwhile, the rotary actuator may be configured to rotate the transducer 360 degrees.

Further, the handpiece may further include a holder configured to hold the plurality of transducers, and the rotary actuator may be configured to rotate the holder.

Meanwhile, the holder may be configured to rotate about an axis passing through an ultrasound focal point of any one of the transducers.

Further, the holder may be configured to rotate about an axis that does not intersect ultrasound focal points of the plurality of transducers.

Meanwhile, the handpiece may include an acceleration sensor, and the controller may control operations of the rotary actuator and/or the plurality of transducers based on a moving velocity of the handpiece measured by the acceleration sensor.

Further, the ultrasound focal points of the plurality of transducers may be formed at different distances from the handpiece.

In addition, there is provided a method of controlling a HIFU device capable of three-dimensional treatment, the method including: receiving a first parameter entered by a user; controlling a rotary actuator to rotate at least one transducer based on the first parameter; and controlling operations of the transducer based on the first parameter while the at least one transducer is rotating.

Meanwhile, the controlling the operations of the transducer may include: calculating a moving velocity of each transducer; and controlling the operations of the transducers independently of each other based on the moving velocities of the transducers.

Meanwhile, the method may further include: identifying a second parameter based on a moving velocity of a handpiece from an acceleration sensor provided in the handpiece, wherein the controlling the rotary actuator includes adjusting an operating amount of the rotary actuator based on the first parameter and the second parameter.

Meanwhile, the controlling the operations of the transducers may include adjusting an operating frequency of each transducer based on the first parameter, the second parameter, and the moving velocity of each transducer.

Meanwhile, the adjusting the operating amount of the rotary actuator may include increasing a rotating velocity as the moving velocity of the handpiece increases.

Meanwhile, the controlling the operations of the transducers may include shortening the operating frequency of the transducer as the moving velocity of the transducer increases.

Further, the controlling the operations of the transducers may include adjusting the operating frequencies of the transducers to be different as the moving velocities of the transducers are different.

In addition, there is provided a three-dimensional treatment method using a high-intensity focused ultrasound (HIFU) device, the method including: receiving a first parameter for a treatment mode entered by a user; pressing a handpiece including a HIFU transducer against skin; and denaturing tissue by focusing ultrasound by the transducer rotating inside the handpiece based on the first parameter.

Meanwhile, the denaturing the tissue may be performed by forming focal points of HIFU at different depths.

Further, the denaturing the tissue may be performed by operating a plurality of transducers, and moving the plurality of transducers at different velocities.

Meanwhile, the method may further include: moving the handpiece on the skin; and setting a second parameter based on a moving velocity of the handpiece, wherein the denaturing the tissue includes moving ultrasound focal points at different depths and at different velocities within tissue based on the first parameter and the second parameter, and focusing ultrasound at different operating frequencies of the transducers.

Meanwhile, the denaturing the tissue may include adjusting a rotating velocity of the transducer based on the second parameter.

Further, the adjusting the rotating velocity of the transducer may include adjusting the rotating velocity of the transducer to be different according to an angle of the transducer based on a moving direction of the handpiece.

Advantageous Effects

According to the disclosure, there are provided a HIFU device capable of three-dimensional treatment, a control method thereof, and a treatment method using the same, in which tissue is three-dimensionally treated, thereby maximizing treatment effects and shortening treatment time.

MODE FOR INVENTION

Figure 1:
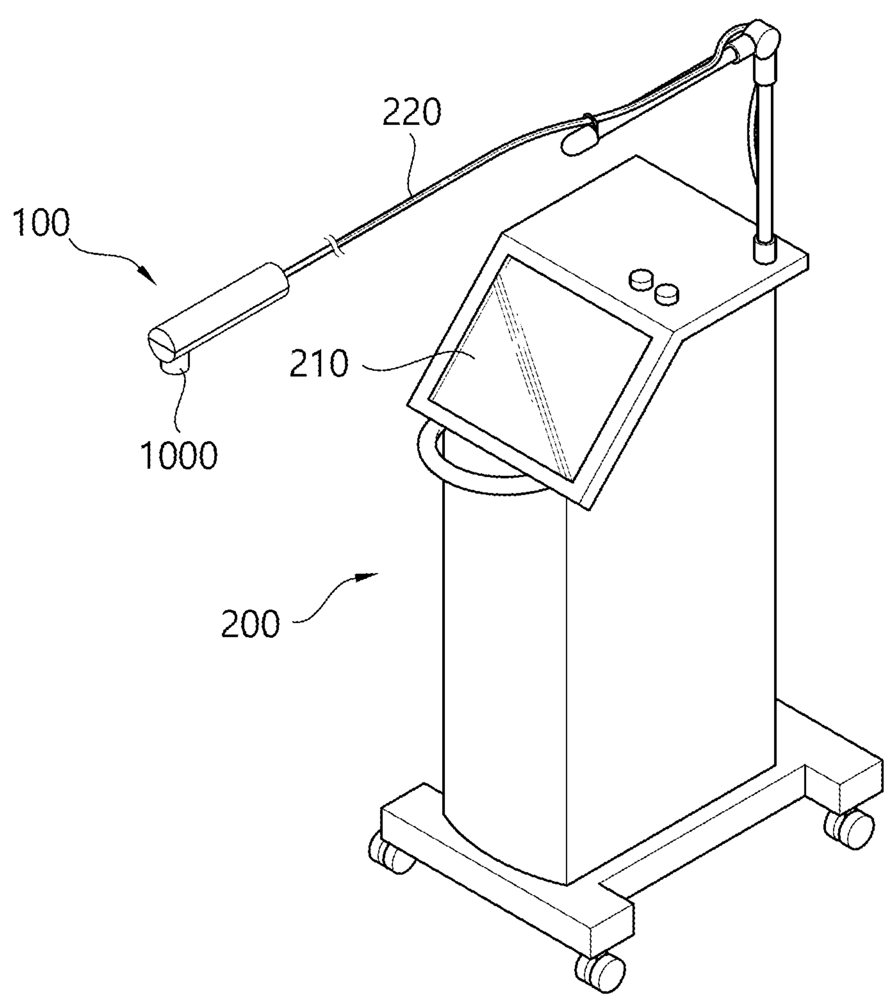
FIG. 1 is a perspective view of a high-intensity focused ultrasound (HIFU) device capable of three-dimensional treatment according to a first embodiment of the disclosure.

Hereinafter, a high-intensity focused ultrasound (HIFU) device capable of the three-dimensional treatment, a control method thereof and a treatment method using the same according to embodiments of the disclosure will be described in detail with reference to the accompanying drawings. Elements described in embodiments set forth herein may be called other names in the art. However, if the elements are similar or identical in terms of their functions, they may be regarded as equivalents even in alternative embodiments. Further, symbols assigned to the elements are given for convenience of description. However, content on the drawings with these given signs do not limit the elements to a range in the drawings. Likewise, even though the elements on the drawings are partially modified according to alternative embodiments, they having functional similarity and identity may be regarded as equivalents. Further, if those skilled in the art recognizes natural involvement of elements, descriptions of the elements will be omitted.

In this specification, descriptions will be made on the premise that treatment means to improvement in wrinkles, tone and textural changes, scars and acne scarring, sagging mucosa, overall rejuvenation, hyperhidrosis, laxity, lifting, tightening, fat reduction, etc. by locally heating skin tissue.

FIG. 1 is a perspective view of a HIFU device capable of three-dimensional treatment according to a first embodiment of the disclosure.

As shown therein, a skin treatment device 1 using HIFU according to the first embodiment of the disclosure may include a main body 200, a handpiece 100, and a cable 220 connecting the main body 200 and the handpiece 100.

The main body 200 may include a power supply, a controller, and a user interface 210, and may be configured to transfer energy for treatment from the power supply to the handpiece 100 and perform control based on a sensing value received from the handpiece 100.

The user interface 210 may be configured to receive inputs for a treatment mode, setting values, etc., to display information for each user, and to display information related to the current treatment. The user interface 210 may include a display, and may for example be configured as a touch-screen so that the input and display of information can be implemented simultaneously.

The handpiece 100 may be configured to be gripped and used by a user, and may include a cartridge 1000 provided at one side to transfer energy to tissue to be treated.

The cartridge 1000 may include a plurality of ultrasound transducers 1410 and 1420, and each of the ultrasound transducers 1410 and 1420 is configured to focus ultrasound energy on one focal point.

Figure 2:
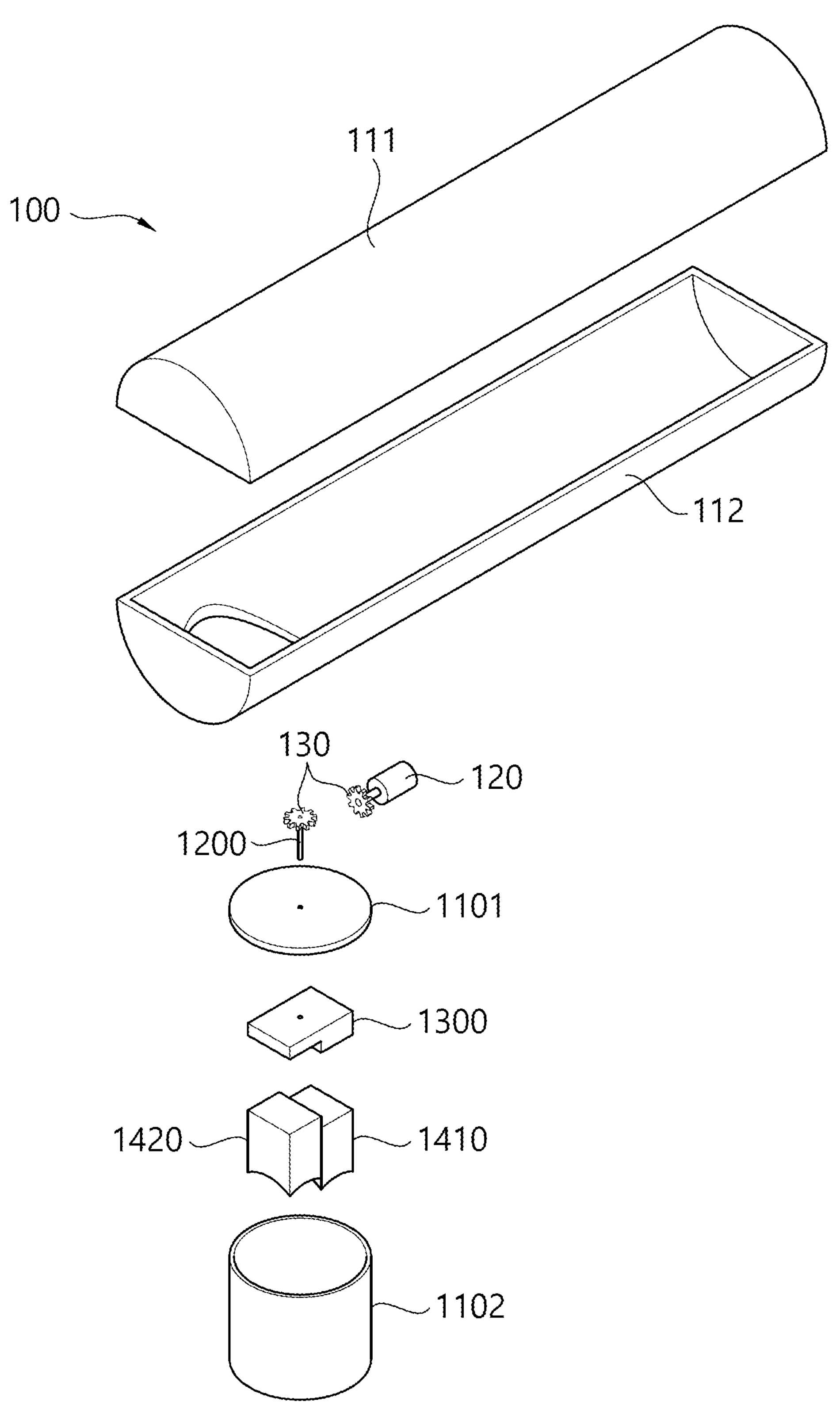
FIG. 2 is an exploded perspective view of a handpiece according to the first embodiment of the disclosure.

FIG. 2 is an exploded perspective view of the handpiece 100 according to the first embodiment of the disclosure Referring to FIG. 2, the handpiece 100 may include an upper casing 111, a lower casing 112, the cartridge 1000, and an actuator 120.

The upper casing 111 and the lower casing 112 may be coupled to each other while forming an inner space therebetween. The inner space defined by the upper casing 111 and the lower casing 112 may accommodate circuitry and the actuator 120 to control transducers 1410 and 1420.

The actuator 120 provides power to rotate the transducers 1410 and 1420. The actuator 120 may be controlled by the controller to control the rotated angle and the rotating velocity of the transducers 1410 and 1420.

The cartridge 1000 may include a cartridge housing 1101 and 1102, the transducers 1410 and 1420, a holder 1300, and a shaft 1200. The cartridge housing may have a space to accommodate the transducers 1410 and 1420 therein. The cartridge housing may include an upper cartridge housing 1101, and a lower cartridge housing 1102. The upper cartridge housing 1101 is formed with a hole through which the shaft 1200 passes. The upper cartridge housing 1101 and the lower cartridge housing 1102 are coupled to each other and configured to accommodate a fluid therein, and may be sealed to prevent the fluid from leaking while the handpiece 100 is in use.

The transducers 1410 and 1420 may include a plurality of transducers, and each of the transducers 1410 and 1420 may be configured to generate ultrasound to be focused on focal points P1 and P2.

The holder 1300 may be configured to hold the plurality of transducers 1410 and 1420. Below the holder 1300, the plurality of transducers 1410 and 1420 are oriented to focus the ultrasound downwardly. Above the holder 1300, the shaft 1200 may be provided.

The shaft 1200 may be provided penetrating the top of the cartridge housing 1101. The shaft 1200 may be configured to rotate together with the holder 1300.

Meanwhile, the actuator 120 of the handpiece 100 may include a motor, and a rotor of the motor and the shaft 1200 of the cartridge 1000 may be coupled by a power transmission mechanism 130. The power transmission mechanism 130 may for example include gears such as bevel gears or the like driving elements to transmit rotational force when the motor is disposed at an angle to the shaft 1200. However, this is merely an example. Alternatively, the power transmission mechanism 130 may be implemented with various known elements for allowing the actuator 1200, such as the motor, to rotate the shaft 1200.

Meanwhile, although not shown, at least one switch (not shown) may be provided for allowing a user to selectively operate the ultrasound transducers 1410 and 1420.

Figure 3:
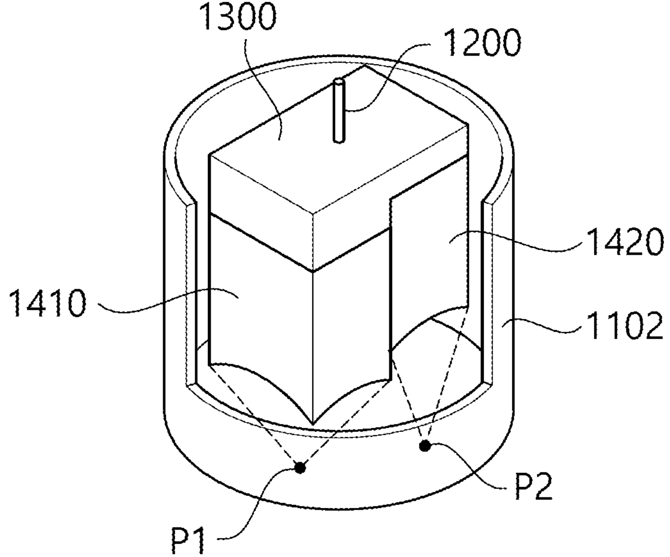
FIG. 3 is a cut-open perspective view showing a transducer in the first embodiment of the disclosure.

FIG. 3 is a cut-open perspective view showing the transducers 1410 and 1420 in the first embodiment of the disclosure.

Referring to FIG. 3, the transducers according to this embodiment may form a pair. When the transducers are configured identically, in other words, when the transducers have the same focal length, the transducers 1410 and 1420 may be provided in different positions on the holder 1300. In other words, the transducers are configured to focus the ultrasound downwardly in FIG. 3. In this case, the focal points P1 and P2 which the ultrasounds are focused may be different in depth. Hereinafter, the focal length will be referred to as 'depth' because the cartridge 1000 transfers ultrasound energy into skin as being in close contact with the skin.

According to an embodiment, even when the transducers 1410 and 1420 forming a pair are provided in the same position on the holder 1300, the difference in depth up to which energy is transferred within the tissue may be substantially implemented by using the transducers 1410 and 1420 different in focal length from each other.

The lower end of the shaft 1200 may be secured to an upper portion of the holder 1300. In this case, the rotational axis of the shaft 1200 may pass between the pair of transducers 1410 and 1420. In this case, when the transducers 1410 and 1420 forming a pair have the same configuration and size, the rotational axis may pass through a midpoint between the focal points of the transducers 1410 and 1420. In other words, distances from the rotational axis to the focal points of the transducers 1410 and 1420 may be the same.

Meanwhile, when the holder 1300 is rotated, the pair of transducers 1410 and 1420 may rotate together simultaneously. When the transducers 1410 and 1420 transfer the ultrasound energy while rotating, treatment spots may be formed in a circular path. Here, the treatment spot refers to at least one area where tissue is denatured by the transferred energy.

Figure 4:
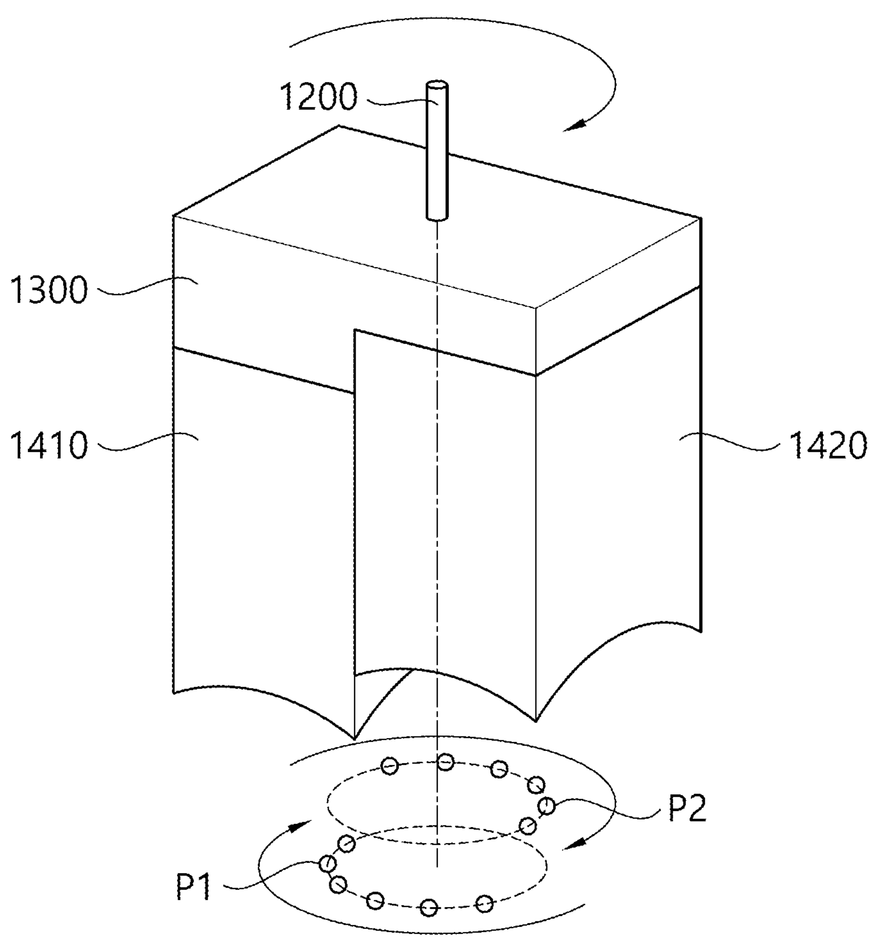
FIG. 4 is a view showing an operating state according the first embodiment.
Figure 5:
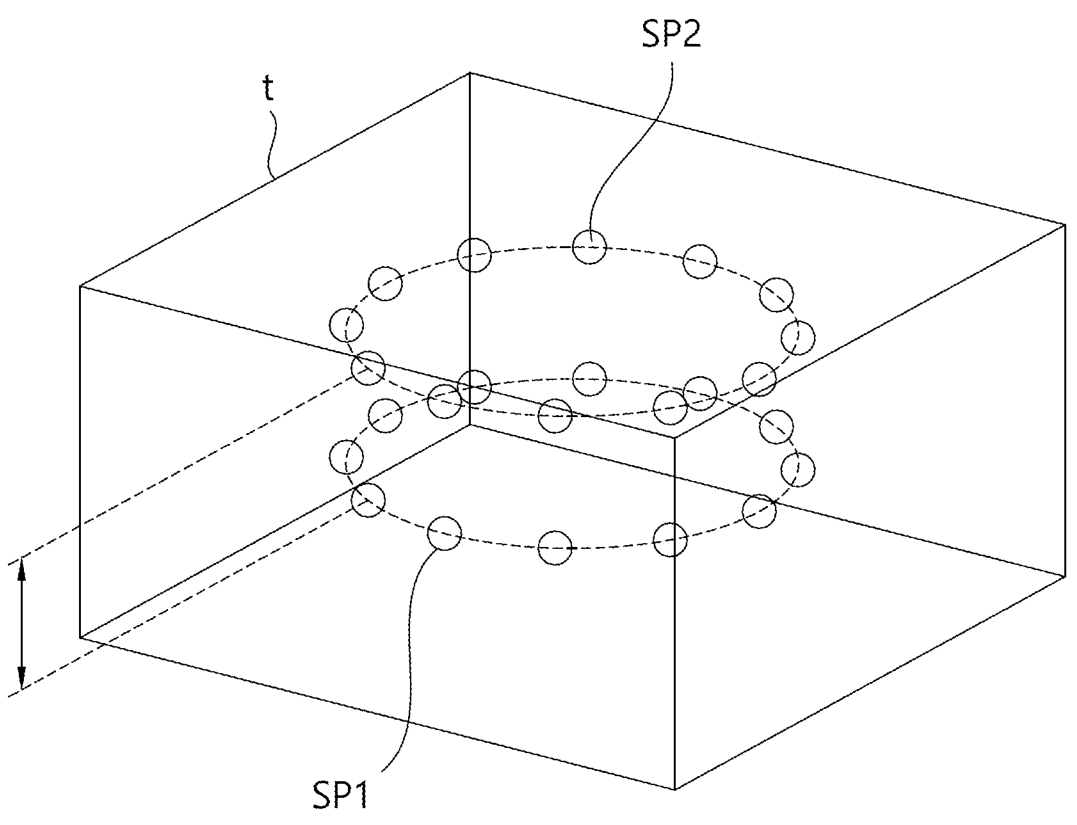
FIG. 5 is a view showing an area treated by rotating a holder once within tissue in the first embodiment.

FIG. 4 is a view showing an operating state according the first embodiment, and FIG. 5 is a view showing an area treated by rotating the holder 1300 once within tissue in the first embodiment.

Referring to FIG. 4, when a user presses the bottom of the cartridge 1000 against skin, the focal points of the transducers 1410 and 1420 may be located within tissue. In other words, the transducers 1410 and 1420 may perform treatment at different depths within the tissue.

Specifically, when the holder 1300 rotates, the pair of transducers 1410 and 1420 rotates about the rotational axis. Thus, a first focal point P1 of a first transducer 1410 moves along a circular path and a second focal point P2 of the second transducer 1420 moves at a position of 180 degrees to the first focal point P1 in the same rotating direction as the first focal point P1 along the circular path. In this case, the transducers are operated to generate ultrasound at predetermined time intervals, the treatment spots are formed at predetermined intervals on the circular path.

FIG. 5 shows treatment spots SP1 and SP2 within tissue t when the holder is completely rotated once inside the cartridge. The first transducer treats deep tissue, forming the first treatment spots SP1 at multiple points along the circular path. Further, the second transducer treats shallow tissue, forming the second treatment spots SP2 at multiple points along the circular path. In other words, by rotating the two transducers once, the treatment spots are formed at different depths at the multiple points in 360 degrees around the rotational axis, thereby achieving the three-dimensional treatment.

Below, alternative examples to the HIFU device capable of the three-dimensional treatment, the control method thereof and the treatment method using the same according to the disclosure will be described with reference to FIGS. 6 to 9C. The following alternative examples may also be implemented including the same elements as those of the foregoing embodiment. In the following alternative examples, two transducers are provided like those of the foregoing embodiment, but the position of the rotational axis is different.

Figure 6:
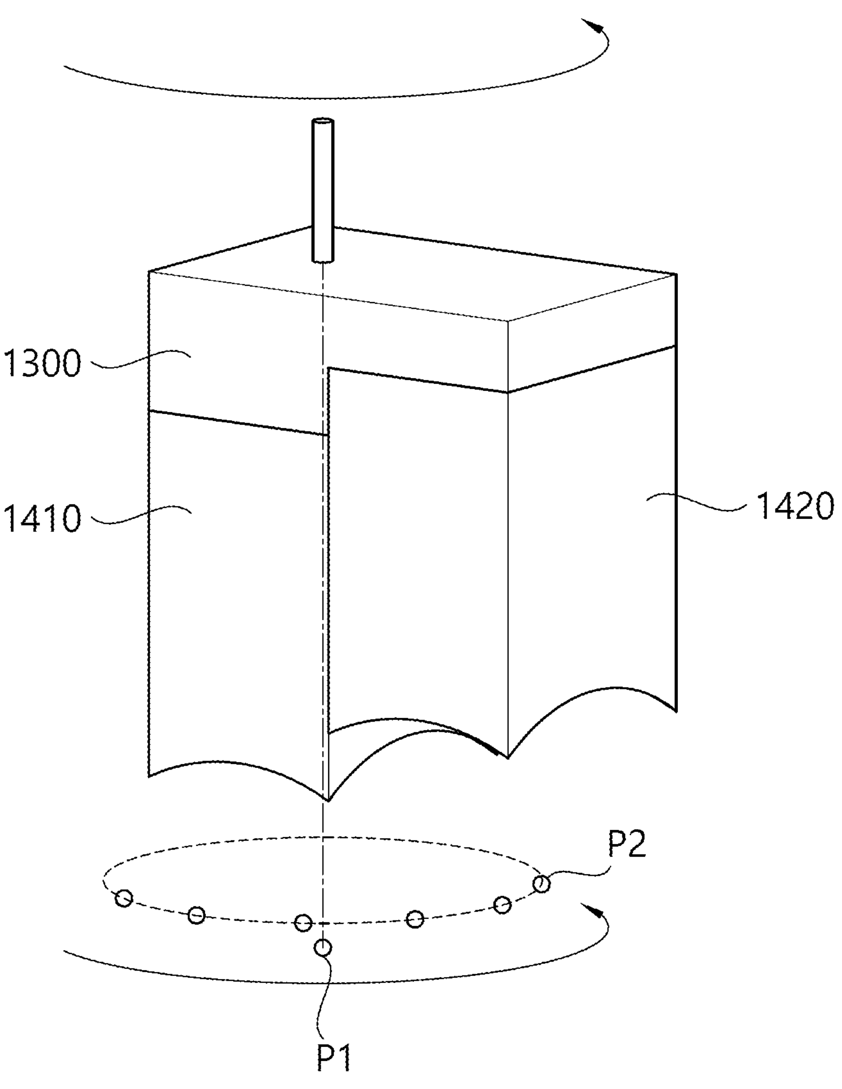
FIG. 6 is a view showing an operating state of a HIFU device capable of three-dimensional treatment according to a second embodiment of the disclosure.

FIG. 6 is a view showing an operating state of a HIFU device capable of three-dimensional treatment according to a second embodiment of the disclosure.

Referring to FIG. 6, the HIFU device 1 capable of the three-dimensional treatment according to the second embodiment of the disclosure may be configured such that the rotational axis passes through the focal point of any one of the transducers. In other words, the focal point of the first transducer for deep treatment may be located on the rotational axis of the holder. To this end, the shaft may be provided above the first transducer 1410 as shown in FIG. 6.

Specifically, when the holder 1300 is rotated by the actuator, the first focal point P1 of the first transducer 1410 may be formed as one point, and the second focal point P2 of the second transducer 1420 may be formed along a circular path having a larger radius than that of the first embodiment.

Figure 7:
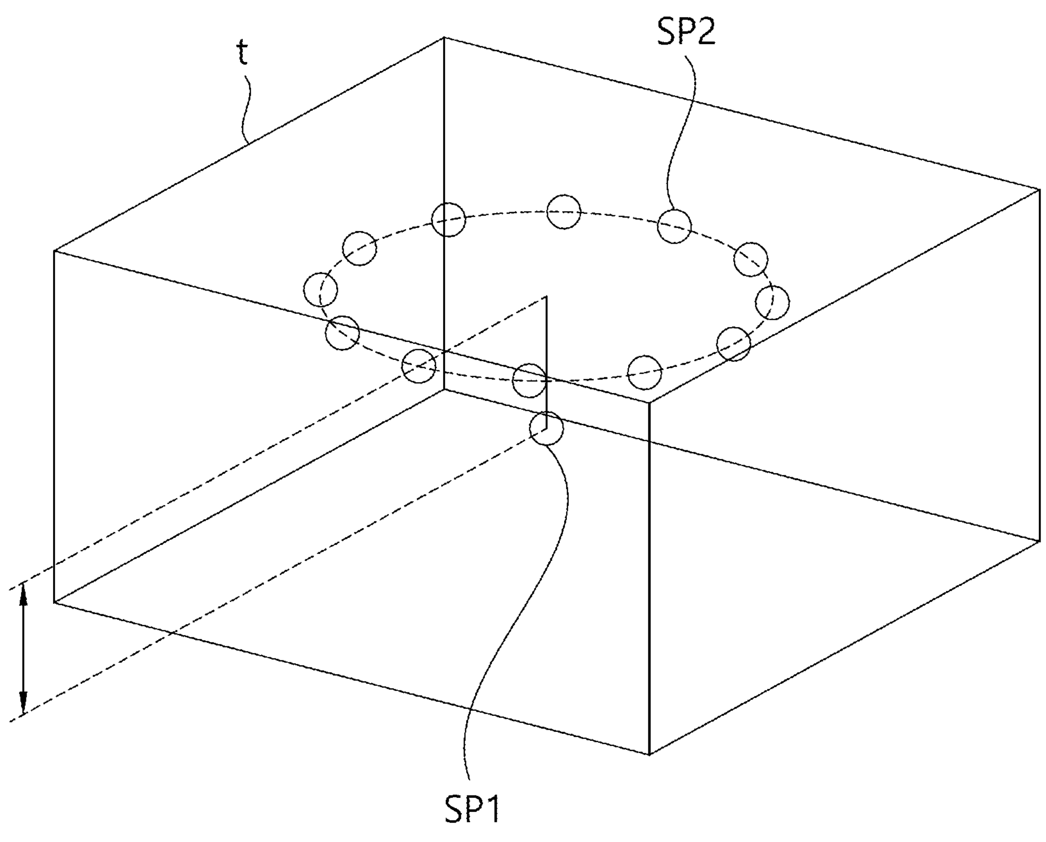
FIG. 7 is a view showing an area treated by rotating a holder once within tissue in the second embodiment of the disclosure.

FIG. 7 is a view showing an area treated by rotating a holder once within tissue in the second embodiment of the disclosure.

Referring to FIG. 7, the period of generating ultrasound may be set to prevent the first transducer 1410 from transferring excessive energy to one first treatment spot SP1. In other words, the first transducer 1410 may transfer ultrasound once while rotating 360 degrees. On the other hand, the second transducer 1420, which treats a large area, may transfer ultrasound energy dozens of times.

Ultimately, the treatment based on one rotation may result in one first treatment spot SP1 and dozens of second treatment spot SP2 corresponding to the circular path, which are formed at different depths.

Below, a third embodiment will be described with reference to FIG. 8.

Figure 8:
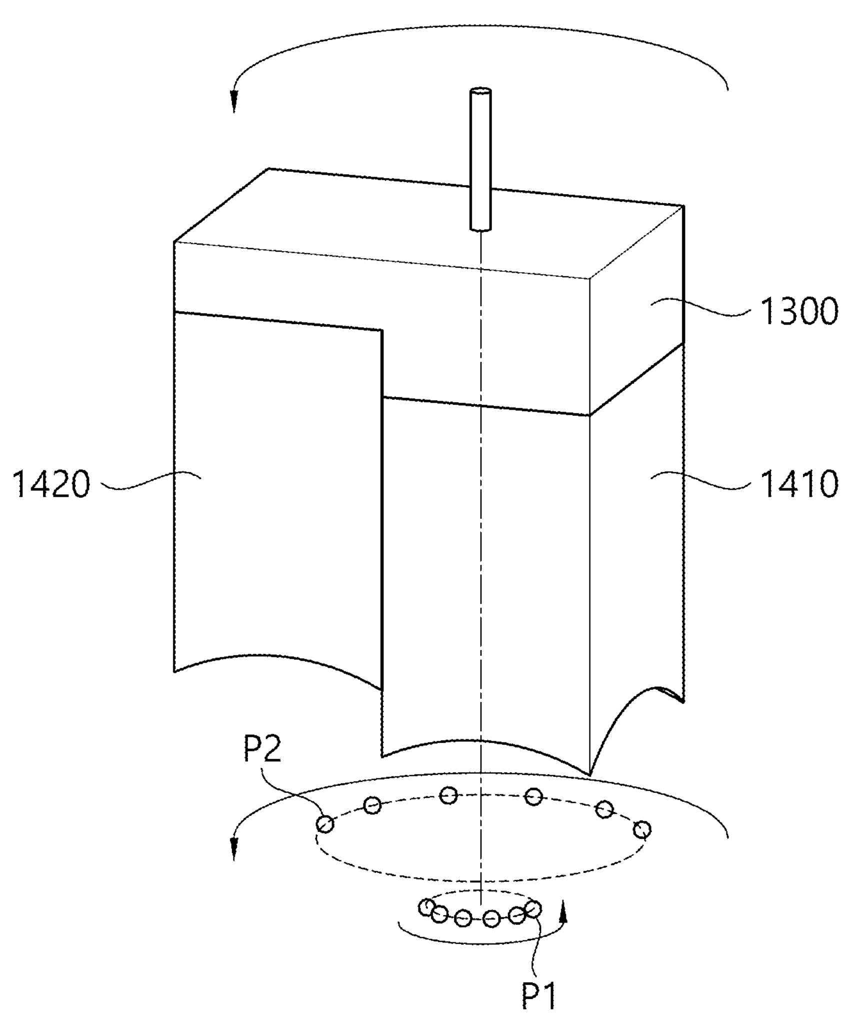
FIG. 8 is a view showing an operating state of a HIFU device capable of three-dimensional treatment according to a third embodiment of the disclosure.

FIG. 8 is a view showing an operating state of a HIFU device capable of three-dimensional treatment according to a third embodiment of the disclosure.

Referring to FIG. 8, the HIFU device capable of the three-dimensional treatment according to the third embodiment of the disclosure may be set such that the focal points of the transducers are different in distance from the rotational axis. In other words, unlike the second embodiment described above, the rotational axis may pass between the focal points of the two transducers 1410 and 1420 without passing through the focal points of the transducers 1410 and 1420.

In this case, the focal points P1 and P2 of the transducers may move along the two circular paths based on the distances between the rotational axis and the focal point of each transducer.

Figure 9A:
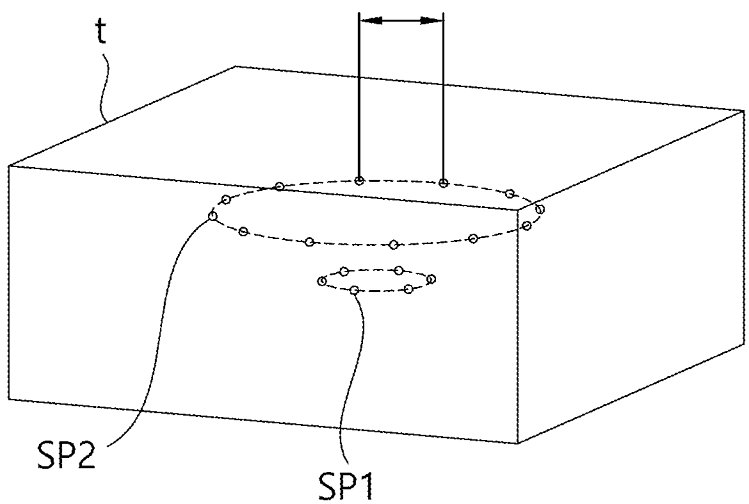
FIGS. 9A, 9B and 9C are views illustrating the concept of treatment areas generated when an ultrasound generation frequency of a transducer is adjusted in the third embodiment.
Figure 9B:
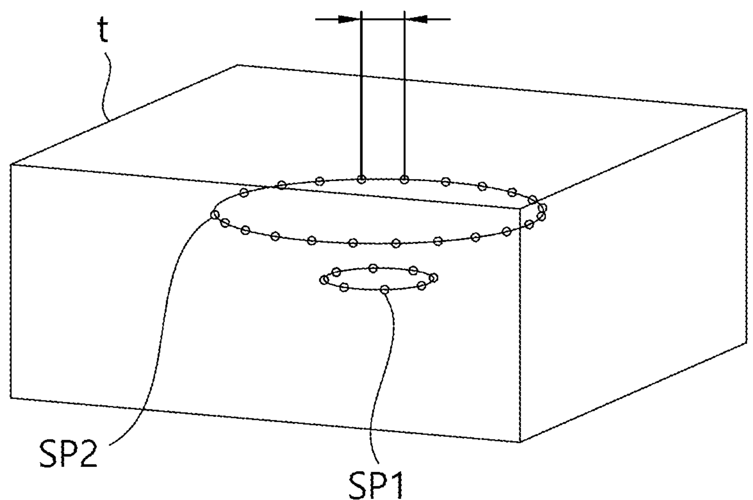
Figure 9C:
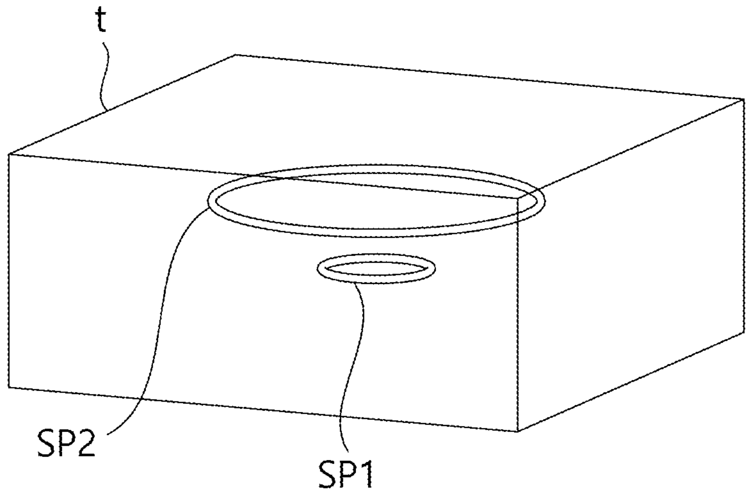

FIGS. 9A, 9B and 9C are views illustrating the concept of treatment areas generated when an ultrasound generation frequency of a transducer is adjusted in the third embodiment.

Referring to FIG. 9A, the first treatment spots SP1 caused by the first transducer of which the focal point has a short distance from the rotational axis are formed along a small circular path. Further, the second treatment spots SP2 caused by the second transducer of which the focal point has a long distance from the rotational axis are formed along a large circular path. In this case, the first treatment spot SP1 and the second treatment spot SP2 are formed at different depths within the tissue t.

In this case, the ultrasound generation frequency of each transducer may be adjusted to keep a uniform treatment interval even when an overall path along which the treatment spots SP1 and SP2 are formed is changed. Here, the frequency refers to not the frequency of the ultrasound energy but an operating frequency at which each transducer is turned on and off. In this case, the operating frequency of the transducer may be adjusted within a range from 1 to several thousand Hz.

For example, the second transducer, which performs treatment along a longer path, may be adjusted to have a higher ultrasound generation frequency than the first transducer. Therefore, a distance between the adjacent treatment spots is maintained even though the treatment spots are formed along the circular paths different in radius from each other.

Meanwhile, the frequencies of the first transducer and the second transducer may be adjusted to increase the intensity of the treatment. In this case, as shown in FIG. 9B, the distance between the first treatment spots SP1 may become narrower, and the distance between the second treatment spots SP2 may also become narrower.

Further, as shown in FIG. 9C, when the intensity of the treatment is increased, the treatment spots SP1 and SP2 are substantially formed not discretely but continuously.

Meanwhile, although not shown, the handpiece may further include an actuator configured to vertically move the position of each transducer. When each actuator adjusts the vertical position of the transducer, the depth of the focal point may be adjusted within tissue. In this case, the depths of the focal points may be adjusted from person to person based on the thickness of skin, the location of a lesion, etc., thereby performing the three-dimensional treatment with the rotating transducers.

Below, a HIFU device capable of three-dimensional treatment according to a fourth embodiment of the disclosure will be described in detail with reference to FIGS. 10 to 15.

Figure 10:
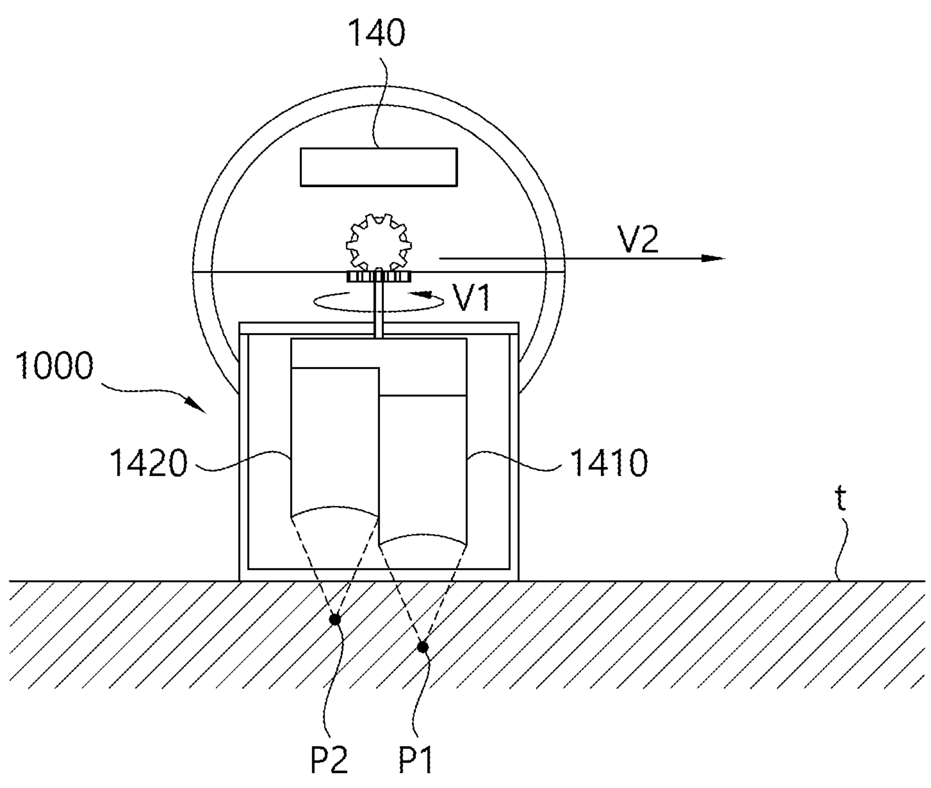
FIG. 10 is a view showing an operating state of a HIFU device capable of three-dimensional treatment according to a fourth embodiment of the disclosure.

FIG. 10 is a view showing an operating state of a HIFU device capable of three-dimensional treatment according to a fourth embodiment of the disclosure.

Referring to FIG. 10, this embodiment may be implemented including the same elements as those of the foregoing embodiments. The HIFU device according to this embodiment may further include an acceleration sensor 140 inside the handpiece. The acceleration sensor 140 may calculate the direction and velocity V2 of the handpiece when a user grips and moves the handpiece (or based on sensing values).

The controller may adjust the rotating velocity and operating frequency of the transducer based on a treatment mode previously entered by a user and the moving direction and velocity V2 of the handpiece measured during the treatment.

Figure 11:
FIG. 11 is a view showing treatment areas based on moving velocities of a handpiece and rotating velocities of a transducer in the fourth embodiment of the disclosure.

FIG. 11 is a view showing treatment areas based on the moving velocities of a handpiece and the rotating velocities of a transducer in the fourth embodiment of the disclosure.

FIG. 11 shows the trajectories of the treatment spot based on differences between the rotating velocity of the transducer and the moving velocity of the handpiece when the transducer transfers ultrasound energy into the tissue at predetermined time intervals.

When the handpiece is not moved (V2=0) during the treatment, the treatment spots are formed along a circular path as shown in the first to third embodiments. However, when the linear velocity V1 of the rotating transducer is greater than the moving velocity V2 of the handpiece (V1>V2), the treatment spots are formed along a curved path. Further, when the linear velocity V1 of the rotating transducer is equal to the moving velocity V2 of the handpiece (V1=V2), the treatment spots are formed along a path having some sharp points. In addition, when the linear velocity V1 of the rotating transducer is smaller than the moving velocity V2 of the handpiece (V1<V2), the treatment spots are formed along a gentle path. In this case, the distance between the treatment spots increases in a similar direction to the moving direction of the handpiece while the focal point of the transducer moves along the circular path. On the other hand, the distance between the treatment spots decreases when the transducer moves in an opposite direction to the moving direction of the handpiece. Therefore, to maintain the constant distance between the treatment spots in this case, it is required to adjust the operating frequency and rotating velocity of the transducer.

Figure 12:
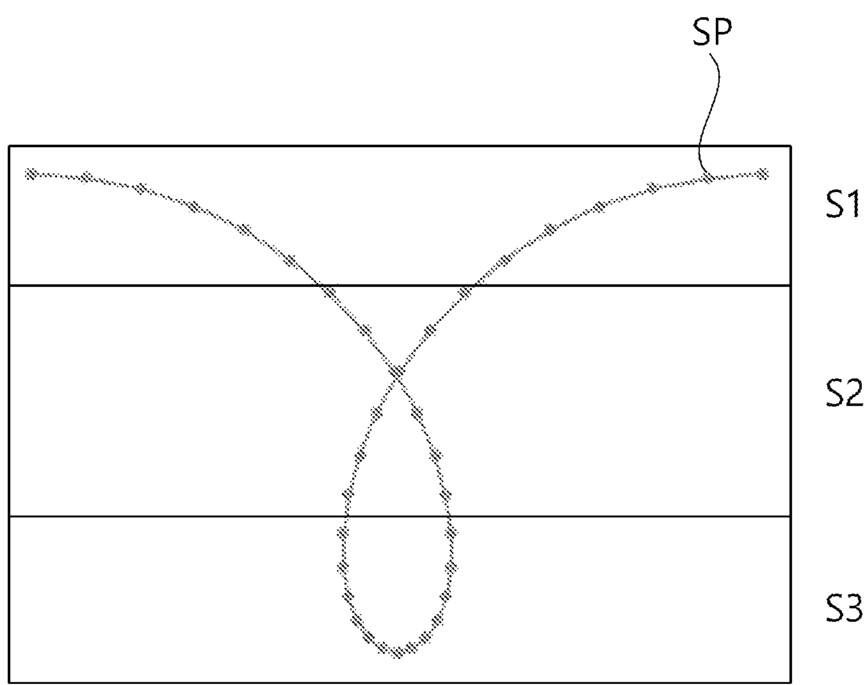
FIG. 12 is a view illustrating the concept of treatment area when the rotating velocity of the transducer is higher than the moving velocity of the handpiece in the fourth embodiment of the disclosure.
Figure 13:
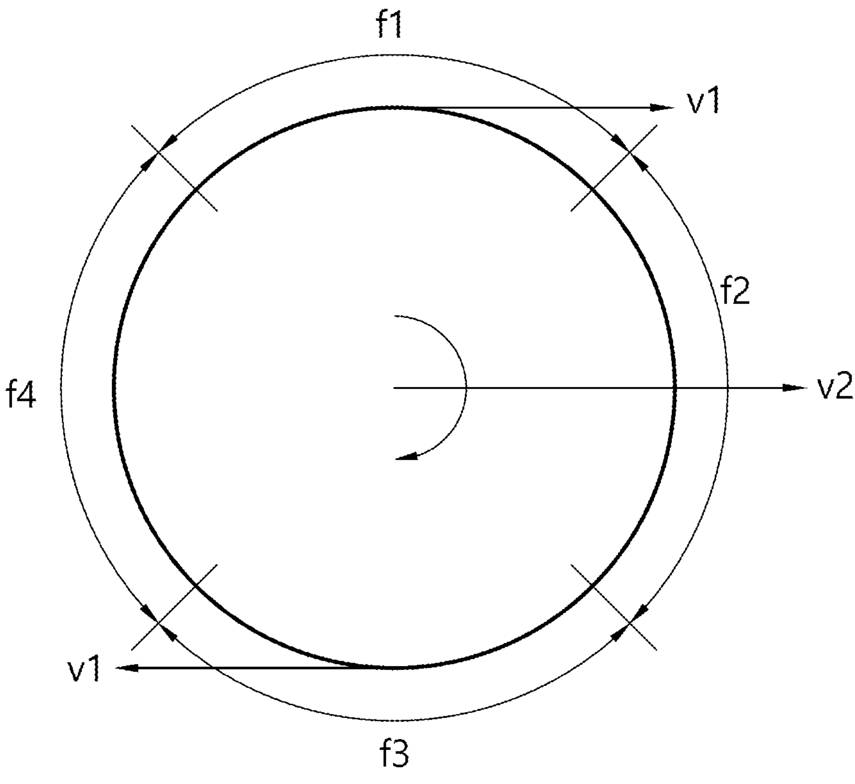
FIG. 13 is a view illustrating the concept of adjusting the frequency for each rotated angle of the transducer according to velocity conditions shown in FIG. 12.

FIG. 12 is a view illustrating the concept of treatment area when the rotating velocity of the transducer is higher than the moving velocity of the handpiece in the fourth embodiment of the disclosure, and FIG. 13 is a view illustrating the concept of adjusting the frequency for each rotated angle of the transducer according to velocity conditions shown in FIG. 12.

Referring to FIG. 12, when the linear velocity V1 of the transducer is smaller than the moving velocity V2 of the handpiece, the distance between the treatment spots is the longest in a first region S1 where vector components in the moving direction of the transducer match those in the moving direction of the handpiece. On the other hand, the distance between the treatment spots in a second region S2 where the moving direction of the transducer is generally perpendicular to the moving direction of the handpiece is slightly decreased as compared with that of the foregoing first region S1. Further, the distance between the treatment spots is the shortest in a third region S3 where the vector components in the moving direction of the transducer are opposite to those in the moving direction of the handpiece.

Referring to FIG. 13, the controller may adjust the frequency corresponding to sections divided according to the angles of the transducer based on the moving direction of the handpiece measured by the acceleration sensor.

In other words, the controller sets a reference angle based on the current moving direction of the handpiece, and calculates the current angle of the transducer relative to the reference angle in order to adjust the ultrasound generation frequency of the transducer according to the sections. Specifically, the controller may adjust the ultrasound generation frequencies f1, f2, f3 and f4 based on four frequencies according to the angles so as to maintain the constant distance between the treatment spots. When the treatment spots are formed as shown in FIG. 13, the controller adjusts the ultrasound generation frequency into f1>f2=f4>f3, thereby maintaining the constant distance between the treatment spots.

Meanwhile, such sections are merely an example. When the frequency is more precisely adjusted according to the rotated angles, an error in the distance between the treatment spots may be minimized. For example, when the moving direction of the handpiece is changed, the moving direction and velocity of the handpiece and the operating frequency of the transducer may be adjusted in real time.

Figure 14:
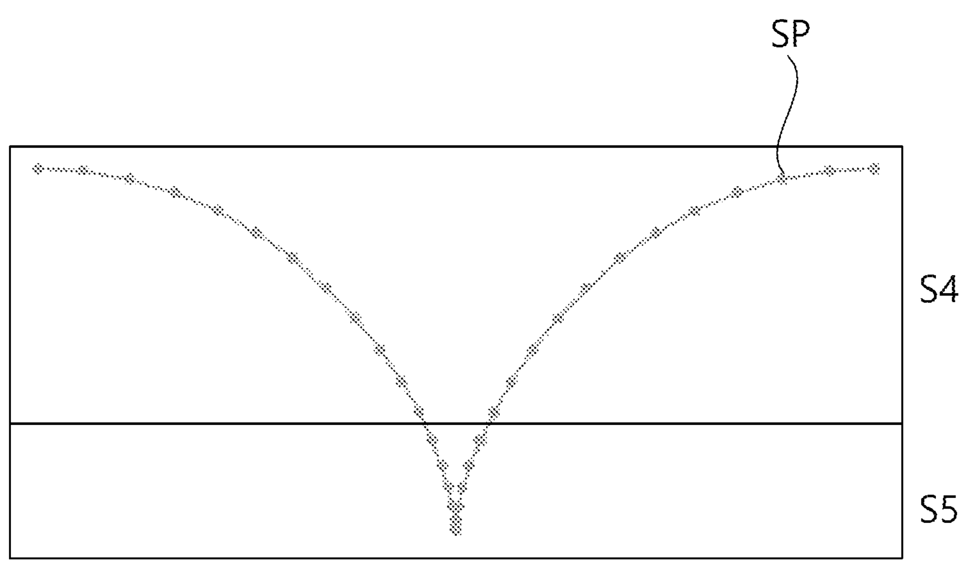
FIG. 14 is a view illustrating the concept of treatment area when the moving velocity of the handpiece is equal to the velocity of the transducer in the fourth embodiment of the disclosure.
Figure 15:
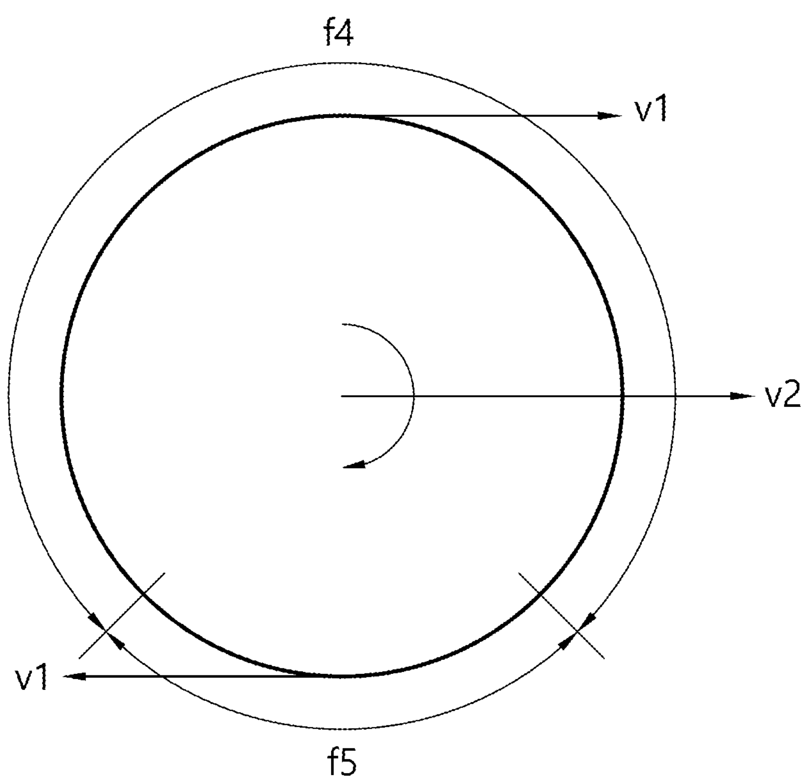
FIG. 15 is a view illustrating the concept of adjusting the frequency for each rotated angle of the transducer according to velocity conditions shown in FIG. 14.

FIG. 14 is a view illustrating the concept of treatment area when the moving velocity of the handpiece is equal to the velocity of the transducer in the fourth embodiment of the disclosure, and FIG. 15 is a view illustrating the concept of adjusting the frequency for each rotated angle of the transducer according to velocity conditions shown in FIG. 14.

Referring to FIG. 14, when the moving velocity of the handpiece matches the moving velocity of the transducer while the operating frequency of the transducer is kept constant, the distance between the treatment spots is generally maintained in a fourth region S4 but the treatment spots become closer and even overlap in a fifth region S5.

Referring to FIG. 15, under the moving condition shown in FIG. 14, the controller may generate the treatment spots at wide intervals by lowering the operating frequency f5 for generating the ultra sound energy on the focal point of the transducer in the fifth region S5 based on the operating frequency f4 in the fourth region S4. As a result, the controller adjusts the operating frequency of the transducer based on the moving velocity of the handpiece and the rotating velocity of the transducer, so that a user can perform uniform treatment in an area to be treated.

Although not shown, the frequency adjustment for the transducer may be performed simultaneously with respect to the plurality of transducers. The distance between the treatment spots is varied depending on the transducers moving at different treatment depths or rotating in different radii. Therefore, to have uniform treatment effect for each treatment depth, the controller may adjust the operating frequency of each transducer in real time.

Meanwhile, the HIFU device according to the foregoing embodiments of the disclosure includes two transducers by way of example. However, such embodiments are merely an example. Alternatively, the HIFU device may include three or more transducers. In this case, the treatment spots are formed at three or more depths to three-dimensionally treat tissue, and the transducers transfer energy to three-dimensionally treat the tissue while moving the focal points of the ultrasound along at least one circular path.

Below, a method of controlling a HIFU device capable of three-dimensional treatment will be described according to an embodiment of the disclosure.

Figure 16:
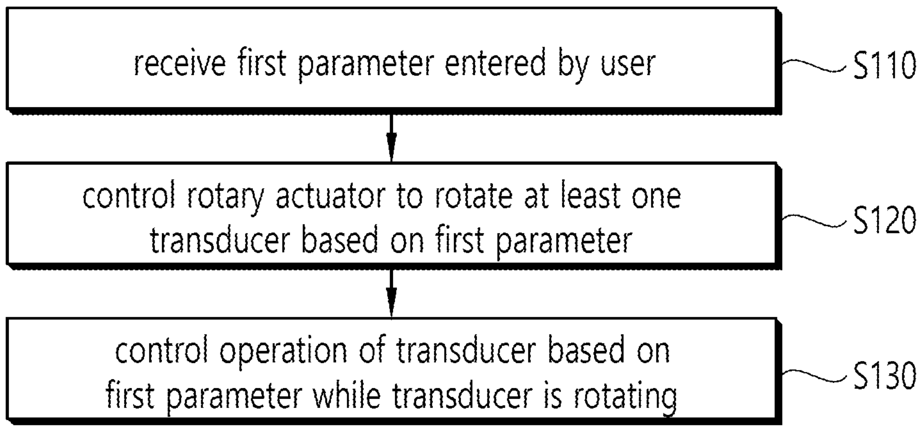
FIG. 16 is a flowchart of how to control a HIFU device capable of three-dimensional treatment according to a fifth embodiment of the disclosure.

FIG. 16 is a flowchart of how to control a HIFU device capable of three-dimensional treatment according to a fifth embodiment of the disclosure.

Referring to FIG. 16, the method of controlling the HIFU device capable of the three-dimensional treatment according to the fifth embodiment of the disclosure may include steps of receiving a first parameter entered by a user (S110), controlling the rotary actuator to rotate at least one transducer based on the first parameter (S120), and controlling the operation of the transducer based on the first parameter while the transducer is rotating (S130).

Step S110 of receiving the first parameter entered by a user refers to step of receiving a treatment mode entered by a user before treatment, for example, information about treatment intensity, treatment time, etc. For example, when the first parameter is a parameter for setting the treatment intensity, the parameter may be to reduce the rotating velocity of the transducer (to be described later) and increase the operating frequency of the transducer.

Step S120 of controlling the rotary actuator to rotate at least one transducer based on the first parameter refers to step of operating the actuator provided in the handpiece and rotating the transducer based on the first parameter. In this case, the transducer may rotate about a preset rotational axis.

Step S130 of controlling the operation of the transducer based on the first parameter while the transducer is rotating refers to step of operating the actuator based on the first parameter to rotate the transducer and generating a control input for operating the transducer at the operating frequency of the transducer set based on the first parameter. In this case, when there are a plurality of transducers, the operating frequencies of the transducers may be different.

Figure 17:
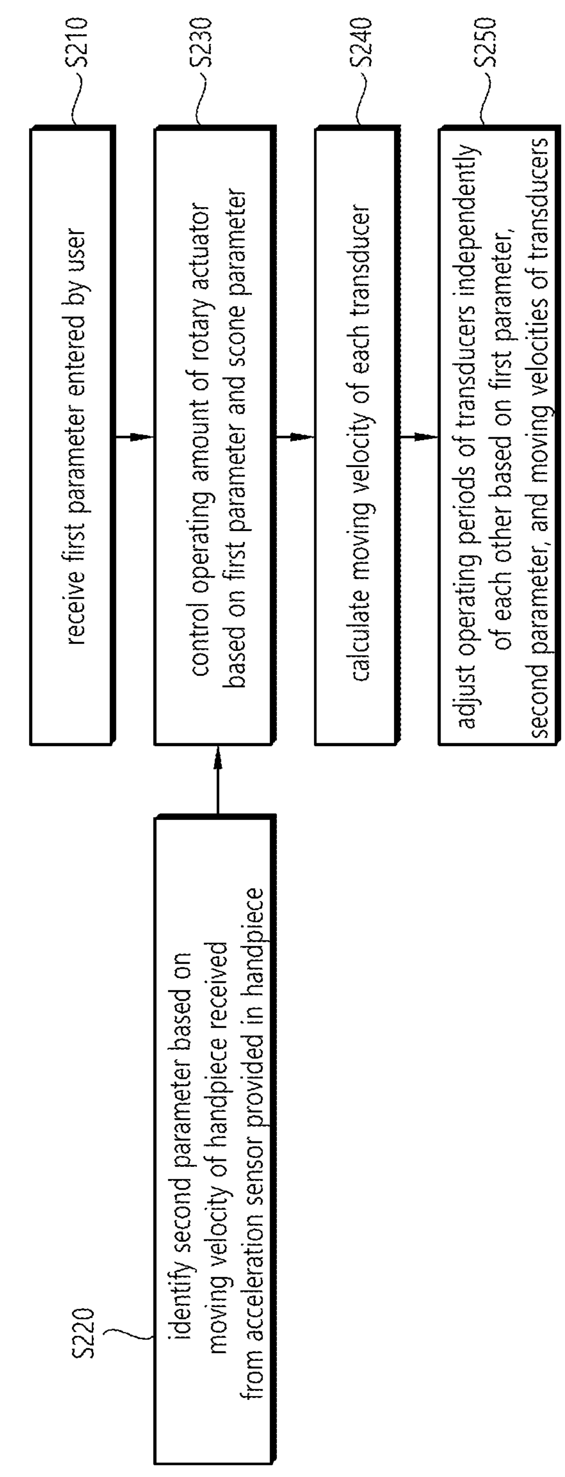
FIG. 17 is a flowchart of how to control a HIFU device capable of three-dimensional treatment according to a sixth embodiment of the disclosure.

FIG. 17 is a flowchart of how to control a HIFU device capable of three-dimensional treatment according to a sixth embodiment of the disclosure.

Referring to FIG. 17, the method of controlling the HIFU device capable of the three-dimensional treatment according to the sixth embodiment of the disclosure may include steps of receiving a first parameter entered by a user (S210), identifying a second parameter based on the moving velocity of the handpiece received from the acceleration sensor provided in the handpiece (S220), controlling the operating amount of the rotary actuator based on the first parameter and the scone parameter (S230), calculating the moving velocity of each transducer (S240), and adjusting the operating periods of the transducers independently of each other based on the first parameter, the second parameter, and the moving velocities of the transducers (S250).

Like the fifth embodiment, the controller identifies the initial moving velocity and operating frequency of the transducer when receiving the first parameter entered by a user.

Then, when it is identified that a user moves the handpiece, step S220 may be performed to identify the second parameter based on the moving velocity of the hand piece received from the acceleration sensor provided in the handpiece.

Then, step S230 of controlling the operating amount of the rotary actuator based on the first parameter and the second parameter may be performed. This step refers to step in which the controller adjusts the previously identified operating amount of the actuator in consideration of the moving velocity of the handpiece.

Step S240 of calculating the moving velocity of each transducer refers to step of calculating the velocity of each transducer moving on skin. In this step, the moving velocity of each transducer having the focal point moving within tissue is calculated based on the distance between the preset rotational center of the transducers and the focal point of each transducer, and the moving velocity of the handpiece.

Step S250 of adjusting the operating periods of the transducers independently of each other based on the first parameter, the second parameter, and the moving velocities of the transducers refers to step of adjusting the operating period (or operating frequency) of each transducer to have a uniform treatment effect on the treatment area passed by the handpiece. In this step, the operation of the transducer is controlled in real time based on the first parameter entered initially and the second parameter identified while the handpiece is in use. With this step, the distance between the treatment spots formed by the transducers for each angle is maintained within a certain range Meanwhile, the foregoing fifth and sixth embodiments may be applied to the HIFU device described above according to the first to fourth embodiments.

Below, a three-dimensional treatment method using a HIFU device according to the disclosure will be described.

Figure 18:
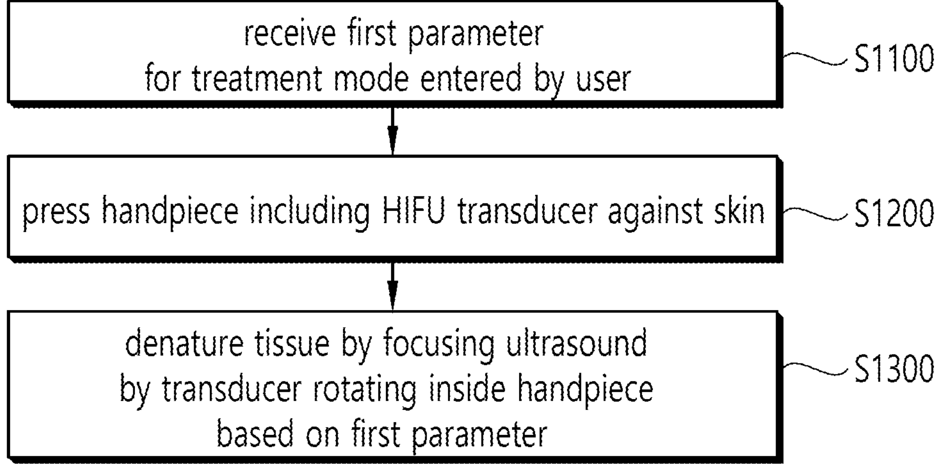
FIG. 18 is a flowchart of a three-dimensional treatment method using a HIFU device according to a seventh embodiment of the disclosure.

FIG. 18 is a flowchart of a three-dimensional treatment method using a HIFU device according to a seventh embodiment of the disclosure.

Referring to FIG. 18, the three-dimensional treatment method using the HIFU device according to the seventh embodiment of the disclosure may include steps of receiving a first parameter for a treatment mode entered by a user (S1100), pressing the handpiece including a HIFU transducer against skin (S1200), and focusing ultrasound by the transducer rotating inside the handpiece based on the first parameter to denature tissue (S1300).

Step S1100 of receiving the first parameter for the treatment mode entered by a user refers to step of setting the treatment mode, i.e., the depth of target tissue for each individual user, and the intensity of the treatment. The intensity of the treatment is directly related to how far apart the treatment spots are formed within one volume.

Step S1200 of pressing the handpiece including a HIFU transducer against skin refers to step of touching the skin with the HIFU device for the treatment. To increase the efficiency of transferring the ultrasound, this step may be performed after applying a gel or the like between the cartridge with the ultrasound transducer and the tissue.

Step S1300 of focusing ultrasound by the transducer rotating inside the handpiece based on the first parameter to denature tissue refers to step of using the plurality of transducers to form the treatment spots at different depths based on the treatment mode entered by a user, and rotating the transducers to generate the treatment area along a curved path. The tissue to which the ultrasound energy is transferred is heated and denatured, and then treated while undergoing a rehabilitative stage.

Figure 19:
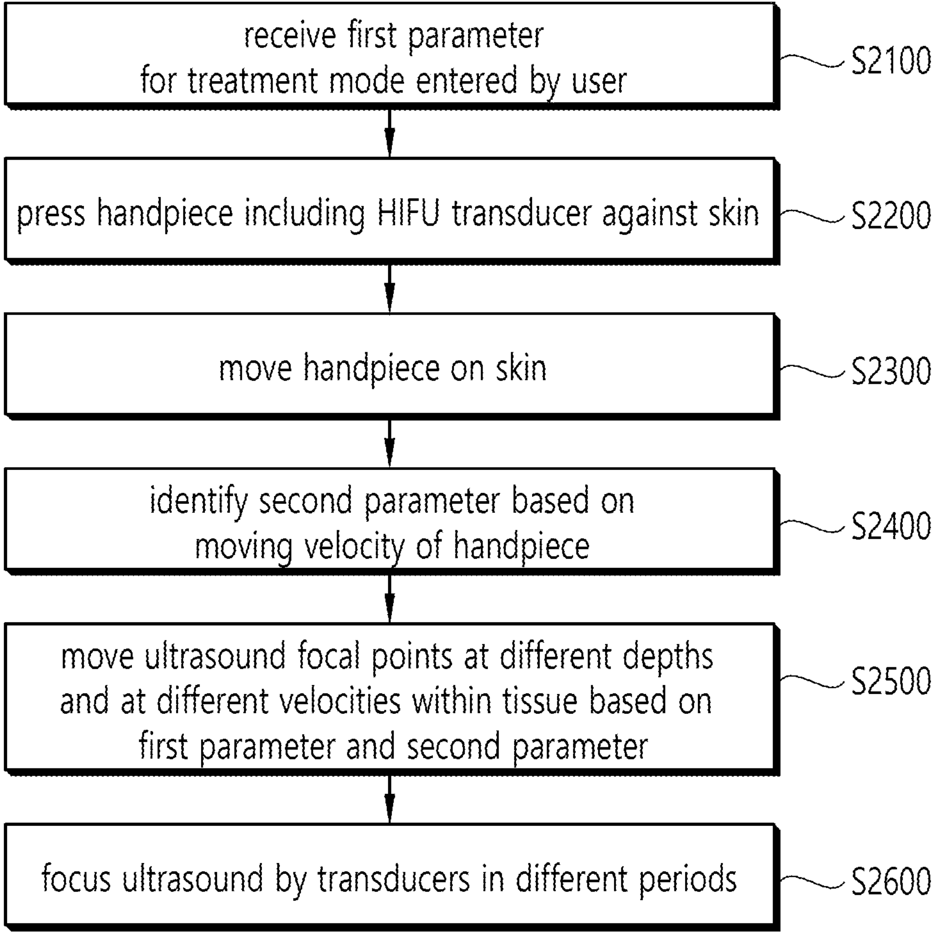
FIG. 19 is a flowchart of a three-dimensional treatment method using a HIFU device according to an eighth embodiment of the disclosure.

FIG. 19 is a flowchart of a three-dimensional treatment method using a HIFU device according to an eighth embodiment of the disclosure.

In this embodiment, the treatment may be performed by calculating the movement of the moving handpiece and adjusting the rotating velocity and the operating frequency of the transducer.

The three-dimensional treatment method using the HIFU device according to the eighth embodiment of the disclosure may include steps of receiving a first parameter for a treatment mode entered by a user (S2100), pressing the handpiece including a HIFU transducer against skin (S2200), moving the handpiece on the skin (S2300), identifying a second parameter based on the moving velocity of the handpiece (S2400), moving the ultrasound focal points at different depths and at different velocities within tissue based on the first parameter and the second parameter (S2500), and focusing ultrasound by the transducers in different periods (S2600).

Step S2100 of receiving a first parameter for a treatment mode entered by a user, and step S2200 of pressing the handpiece including a HIFU transducer against skin may be the same as those in the seventh embodiment.

Step S2300 of moving the handpiece on the skin (S2300) refers to step of moving the handpiece to change a treatment position while a user touches target tissue with the handpiece. In this case, a user may move the handpiece in any direction and at any velocity.

Step S2400 of identifying a second parameter based on the moving velocity of the handpiece refers to step of receiving information about the moving direction and moving velocity of the handpiece from the acceleration sensor provided in the handpiece, and setting the second parameter for controlling the operations of the transducer based on the received information. In this step, the second parameter may be calculated by a computer in real time even though it is not directly entered by a user.

Step S2500 of moving the ultrasound focal points at different depths and at different velocities within tissue based on the first parameter and the second parameter refers to step of adjusting the rotating velocity of the transducer in the cartridge so as to have a uniform treatment effect even though the handpiece is moved by a user. In this case, when the transducers rotate in different radii, the focal points of the transducers move at different velocities.

Step of focusing ultrasound by the transducers in different periods (S2600) refers to step of adjusting the operating frequencies of the transducers so as to maintain the distance between the treatment spots when the focal points of the transducers move at different depths and at different velocities. In this case, the velocity of the transducer is identified by adding the moving velocity of the handpiece thereto. The high moving velocity of the transducer causes a high operating frequency, and the low moving velocity of the transducer causes a low operating frequency. Therefore, the treatment spot where the tissue is denatured may be formed at multiple points, at different depths, and at uniform intervals.

Meanwhile, steps of moving the handpiece on the skin, identifying the second parameter based on the moving velocity of the handpiece, moving the ultrasound focal points at different depths and at different velocities within the tissue based on the first parameter and the second parameter, and focusing ultrasound by the transducers in different periods may be performed repeatedly during one treatment period of the user, and the second parameter may be updated repeatedly.

| [Reference Numerals] | |
|---|---|
| 1: | the HIFU treatment device |
| 100: | handpiece |
| 111: | upper casing |
| 112: | lower casing |
| 120: | actuator |
| 130: | power transmission mechanism |
| 140: | acceleration sensor |
| 200: | main body |
| 210: | user interface |
| 220: | cable |
| 1000: | cartridge |
| 1100: | tip cover |
| 1200: | shaft |
| 1300: | holder |
| 1410: | first transducer |
| 1420: | second transducer |
| P1: | first transducer focal point |
| P2: | second transducer focal point |
| t: | tissue |

The invention claimed is:

1. A high-intensity focused ultrasound (HIFU) device capable of three-dimensional treatment, comprising:

a body comprising a power supply and a controller; and a handpiece connected to the body and comprising a plurality of transducers configured to generate HIFU, the handpiece comprising a rotary actuator configured to rotate at least one of the transducers, wherein the handpiece comprises an acceleration sensor generating a moving velocity of the handpiece, and the controller controls a rotating velocity of the rotary actuator or an operating frequency of each of the plurality of transducers based on the moving velocity of the handpiece generated by the acceleration sensor.

2. The HIFU device of claim 1, wherein the rotary actuator is configured to rotate the transducer 360 degrees.

3. The HIFU device of claim 2, wherein the handpiece further comprises a holder configured to hold the plurality of transducers, and the rotary actuator is configured to rotate the holder.

4. The HIFU device of claim 3, wherein the holder is configured to rotate about an axis passing through an ultrasound focal point of any one of the transducers.

5. The HIFU device of claim 3, wherein the holder is configured to rotate about an axis that does not intersect at least one of ultrasound focal points of the plurality of transducers.

6. The HIFU device of claim 1, wherein the controller varies the rotating velocity of the rotary actuator, or the operating frequency of each of the plurality of transducers, or both, with the moving velocity of the handpiece so as to maintain a distance between subsequent ones of treatment spots formed by the plurality of transducers.

7. The HIFU device of claim 5, wherein the ultrasound focal points of the plurality of transducers are formed at different distances from the handpiece.

8. The HIFU device of claim 7, wherein the plurality of transducers form treatment spots at different depths, and the controller adjusts the rotating velocity of the rotary actuator and the operating frequency of each of the transducers so as to maintain a distance between subsequent ones of the treatment spots at each depth.

* * * * *